United States Patent [19]

Coppens

[11] 4,345,031
[45] Aug. 17, 1982

[54] PROCESS FOR THE MANUFACTURE OF ALDONIC ACIDS BY AN ENZYMATIC METHOD

[75] Inventor: Guillaume Coppens, Brussels, Belgium

[73] Assignee: Solvay & Cie., Brussels, Belgium

[21] Appl. No.: 112,348

[22] Filed: Jan. 15, 1980

[30] Foreign Application Priority Data

Jan. 22, 1979 [FR] France ................. 79 01861

[51] Int. Cl.³ ............................................ C12P 7/58
[52] U.S. Cl. ................................... 435/137; 435/818
[58] Field of Search .................... 435/137, 818

[56] References Cited

U.S. PATENT DOCUMENTS

| 2,351,500 | 6/1944 | Moyer | 435/137 |
| 2,758,934 | 8/1956 | Scott | 435/137 |
| 3,576,718 | 4/1971 | Ziffer et al. | 435/137 |
| 3,669,840 | 6/1972 | Hatcher | 435/137 |
| 3,862,005 | 1/1975 | Miyake et al. | 435/137 |
| 3,935,071 | 1/1976 | Bergmeyer et al. | 435/137 |

Primary Examiner—R. B. Penland
Attorney, Agent, or Firm—Spencer & Kaye

[57] ABSTRACT

A process for the preparation of an aldonic acid from the corresponding ose, comprising enzymatically oxidizing the ose in a reaction mixture containing oxygen. The molar ratio of oxygen to ose in the reaction mixture is greater than 0.1.

5 Claims, 2 Drawing Figures

PROCESS FOR THE MANUFACTURE OF ALDONIC ACIDS BY AN ENZYMATIC METHOD

BACKGROUND OF THE INVENTION

The present invention relates to a process for the manufacture of aldonic acids by an enzymatic method, by oxidising the corresponding oses.

It is known to oxidise oses to the corresponding aldonic acids by an enzymatic method, by employing the enzymes which are specific for these reactions and are generally referred to as oxidases. Thus, glucose is oxidised to gluconic acid with the aid of glucose oxidase. Although very selective, this reaction nevertheless exhibits the disadvantage that it gives a low degree of conversion per unit of enzyme employed, and this results in a very low productivity and makes the process rather uneconomic.

SUMMARY OF THE INVENTION

The object of the present invention is to provide a process for the manufacture of aldonic acids by oxidising the corresponding oses, which process does not exhibit the disadvantages of the conventional processes and makes it possible, in particular, substantially to improve the productivity.

For this purpose, the invention relates to a process for the manufacture of aldonic acids by oxidising the corresponding oses by an enzymatic method, using oxygen, in accordance with which process the molar ratio of oxygen to ose in the reaction mixture is kept above 0.1.

DETAILED DESCRIPTION OF THE INVENTION

Figure 1:
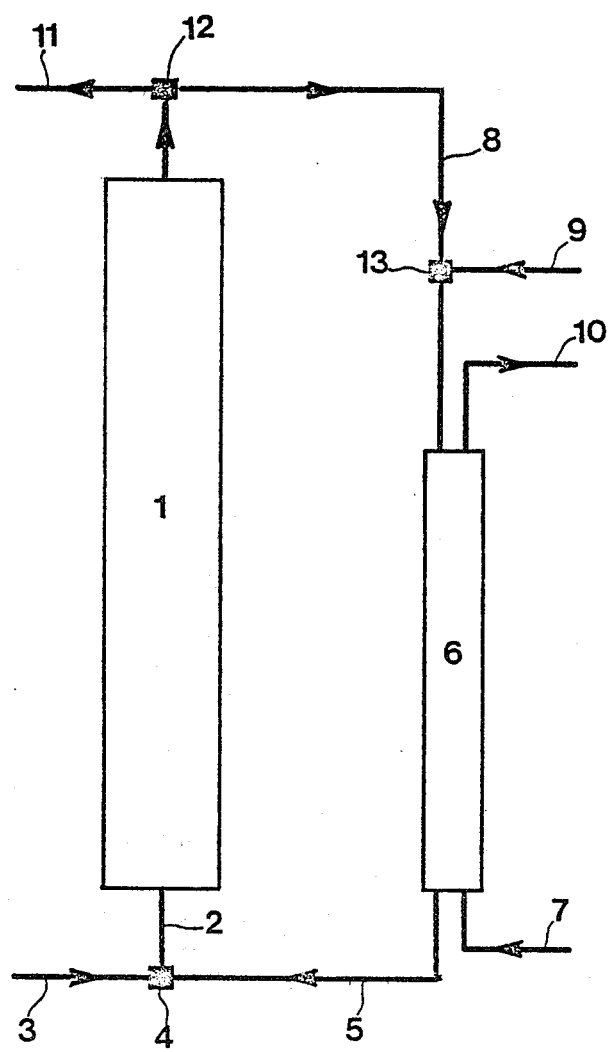
FIGS. 1 and 2 illustrate schematic representations of apparatus in which the process of the present invention can be carried out.

In the process of the present invention, a molar ratio of oxygen to ose of more than 0.2 is preferably used. Good results have been obtained when this molar ratio is between 0.2 and 50. Molar ratios of more than 50 are also suitable but are less advantageous from an economic point of view.

The oxygen used to oxidise the ose to the corresponding aldonic acid can be employed in various forms. In general, oxygen gas is dissolved in the reaction mixture. The oxygen can be employed in the form of pure oxygen or in the form of mixtures of oxygen with inert gases.

In general, a gaseous mixture containing essentially oxygen, preferably in a proportion of at least 90% by weight, is used.

The amount of oxygen dissolved in the medium is generally more than 20 mg/liter. Advantageously, the conditions used are such that the amount of oxygen dissolved in the reaction medium is between 40 and 10,000 mg/liter. The oxygen partial pressures are thus fairly high and are generally at least 0.5 bar. They are preferably between about 1 and 100 bars. Good results have been obtained by using pressures of 3 to 80 bars.

The present invention applies to the oxidation of various types of oses. Thus, it is possible to oxidise glucose, galactose and lactose. Excellent results have been obtained by applying the process of the invention to the oxidation of glucose to gluconic acid.

The process according to the invention can be applied to the oxidation of pure oses or of mixtures of oses. In the latter case, it is possible selectively to oxidise one of the oses with the aid of the enzyme which is specific for the reaction. Thus, in the case of glucose, the invention can be applied to the selective oxidation of the glucose present in mixtures which also contain other sugars such as fructose, galactose and di-, tri- and oligosaccharides in general (maltose, cellobiose, raffinose and the like).

Oxidation of oses to the corresponding aldonic acids is carried out by an enzymatic method with the aid of the oxidases which are specific for the reactions in question. The enzymes can be in various forms, that is to say either in the form of free enzymes or in the form of immobilised enzymes or also contained in cells, the latter being the case of, for example, micro-organisms. Good results have been obtained when employing immobilised enzymes.

All the immobilisation methods which are in themselves known can be used. Various immobilisation techniques have been proposed in the book Immobilized Enzymes, CRC Press, 1974, by O. Zaborsky. Thus, the enzymes can be fixed, in particular, by physical adsorption to a support, by trapping in matrices, inclusion or microencapsulation, by forming a covalent bond between the support and the enzyme, or by co-crosslinking. A particularly appropriate technique formed the subject of Patent Application 79/01,054, filed in France on 12.1.1979 by Solvay and Cie.

The amount of enzyme employed can vary within wide limits. It depends on the nature of the enzyme, the technical grade used and also the form in which it is employed (namely whether or not it is immobilised). In the case of the oxidation of glucose, the glucose oxidase is generally used at a rate of about 0.1 to 10,000 international units per gram of glucose to be converted. Preferably, these amounts are between 1 and 1,000 international units per gram of glucose to be converted.

The reactions involving oxidation of oses to corresponding aldonic acids are generally carried out in a solvent medium. Various solvents can be used for this purpose. Water, by itself or mixed with other solvents which are inert with respect to the reaction, such as alcohols, is generally used as the solvent. Good results have been obtained by using water as the solvent.

In addition to the reactants and the other constituents which may be present in the starting ose, the reaction products, the solvents and the enzyme, the reaction mixture can also contain other constituents. Amongst the latter, there may be mentioned agents for adjusting the pH, agents for separating off or neutralising the aldonic acids formed, bactericidal or fungicidal agents such as ethylene oxide (for controlling possible bacterial pollution), and additives which make it possible to improve the activity of the enzyme. If necessary, agents for removing the hydrogen peroxide formed can also be added. Catalase is very suitable for this purpose.

The pH is usually kept within certain limits, which are chosen in accordance with the nature of the enzyme which is specific for the reaction, in order to prevent degradation or deactivation of the enzyme. Thus, in the case of the oxidation of glucose to gluconic acid, the pH is generally kept at a value of between 4.2 and 8. If the enzyme is immobilised, it is preferred to use pH values of between 5.0 and 8. If, on the other hand, a free enzyme is employed, pH values of between 4.2 and 7 are preferably used.

The various known techniques can be used to keep the pH at the desired value. Thus, buffers can be added to the medium. It is also possible to neutralise the aldonic acid, as it is formed, by adding a base. Amongst the bases which can be used, there may be mentioned alkali metal and alkaline earth metal hydroxides and carbonates, such as sodium hydroxide or potassium hydroxide and sodium carbonate or calcium carbonate, and also organic bases. Good results have been obtained by neutralising the aldonic acid with sodium hydroxide or carbonate. Finally, the gluconic acid can be withdrawn continuously from the reaction mixture by various techniques which are in themselves known, such as electrodialysis, the use of ion exchange resins or precipitation.

The reaction temperature is chosen in accordance with the nature of the specific enzyme employed. The optimum operating temperatures of the enzyme are preferably used. In the case of the oxidation of glucose to gluconic acid with the aid of glucose oxidase, temperatures between 0° and 60° C., and most frequently between 0° and 50° C., are generally used. Good results have been obtained by using temperatures between 0° and 35° C.

The process according to the invention can be carried out continuously or discontinuously. In industry, reactors which operate continuously are generally used. These reactors can be of various types which are in themselves known. Thus, the process can be carried out in mixer reactors or in tubular reactors referred to as "methodical reactors" or "integral reactors". It is possible to use a single reactor or several reactors arranged in series or in parallel. In industry, if it is desired to carry out the process continuously, it is advantageous to have several reactors so that the enzyme charge in one reactor can be renewed without interrupting the entire production.

When employed in the immobilised form, the enzymes can be arranged in the reactors in the form of a fixed bed or a fluidised bed or also in the form of a moving bed or a turbulent bed. The immobilised enzymes can be completely immersed in the liquid reaction mixture or it is also possible to cause the latter to run over the immobilised enzymes.

When the enzymes are employed in the free form, mixer reactors are generally used. If they operate continuously, these reactors are generally provided with devices for preventing the enzyme from leaving the reactor during the removal of production. These devices can be filters used for ultrafiltration. After the reaction, the enzymes can be separated from the reaction mixture in accordance with various techniques which are in themselves known, such as decantation or filtration.

The reactants can be introduced directly into the reactor containing the enzyme. It is also possible to prepare the solution, containing the ose to be oxidised and the oxygen, in saturators or mixer/saturators which are separate from the reactor. Other techniques can also be envisaged.

The materials used to construct the equipment required for carrying out the process of the invention are of diverse types. In general, the materials used are corrosion-resistant and, if necessary, pressure-resistant. Thus, it is possible to use tantalum reactors, Inconel reactors or reactors which have been enamelled or coated with a corrosion-resistant substance.

Figure 2:
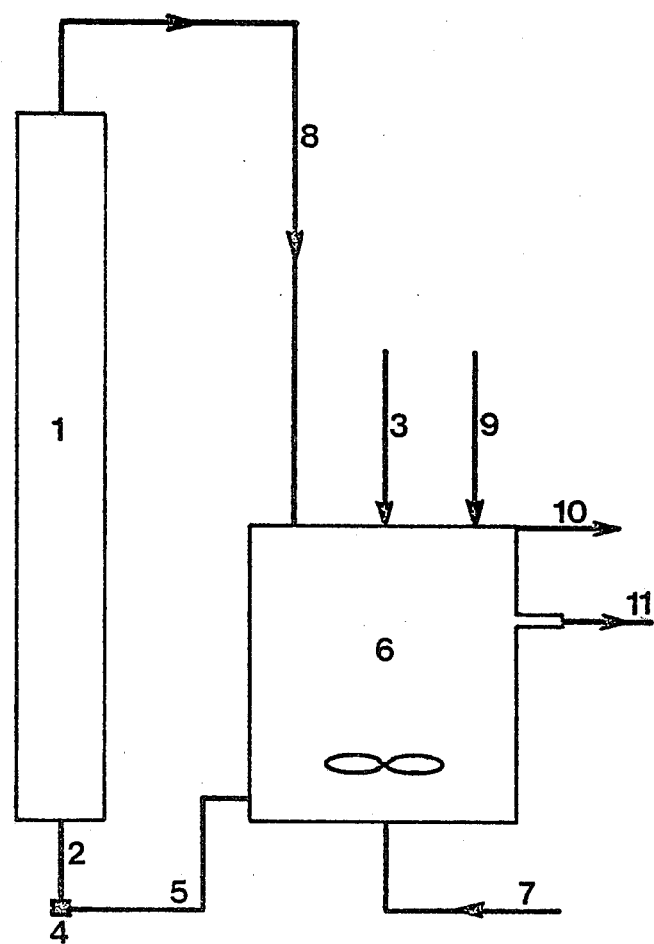

The process according to the invention can be carried out in equipment such as that represented schematically in the attached FIGS. 1 and 2, which figures show embodiments of the process according to the invention.

FIG. 1 shows a reactor 1 in which immobilised enzymes are arranged. The reactor is fed via 2 with a reaction mixture containing the ose, the solvent and oxygen. This mixture originates from the mixer 4 which is fed with ose via 3 and with a solution saturated with oxygen via 5.

The solution saturated with oxygen is obtained in the saturator 6 by bubbling oxygen, introduced via 7, through the recycled solution which originates from the reactor 1 and is brought via 8. The excess oxygen leaves the saturator 6 via 10.

The recycled solution originating from the reactor is neutralised at 13 by adding a base via 9.

Part of the recycled solution, which constitutes the production, is removed continuously at 12 via 11.

FIG. 2 shows similar equipment to that in FIG. 1, in which equipment the ose is introduced directly via 3, and the neutralising base is introduced via 9, into a mixer/saturator 6. The excess oxygen leaves the mixer/saturator via 10 and the production is collected by overflow via 11.

According to the processes represented schematically in FIGS. 1 and 2, a solution, which essentially contains the solvent, the unconverted ose and the partially neutralised aldonic acid, is circulated continuously. The proportion of partially neutralised aldonic acid in the solution can vary within wide limits. In general, the process is carried out under concentration conditions which are close to saturation. Thus, when oxidising glucose to gluconic acid with the aid of glucose oxidase, if a sodium derivative is used as the neutralising agent, the concentration of sodium gluconate in the solution can reach 500 g liter$^{-1}$, depending on the temperature, and is generally between 50 and 450 g liter$^{-1}$.

The process of the invention is especially suitable for selectively converting one particular ose in a mixture of oxes. Thus, the process of the invention can advantageously be applied to the selective conversion of glucose in mixtures of sugars, such as, for example, the mixtures of glucose and fructose obtained by hydrolysing sucrose or by isomerising glucose, or the mixtures of glucose and fructose obtained from polysaccharides rich in fructose, such as inulin and its derivatives (in these cases, the concentration of gluconic acid, or gluconate, can vary from 1 to 200 g/liter). This technique, followed by separation of the gluconic acid or its salt from the mixture, makes it possible to separate off pure fructose. This product can itself be used for dietetic or pharmaceutical preparations or in foodstuffs for diabetics.

The process of the invention exhibits the advantage that it makes it possible to obtain solutions having particularly high concentrations of aldonic acids (or of their corresponding salts), which simplifies the subsequent separation steps in particular. Moreover, for a given type of enzyme, the process makes it possible to obtain substantially better yields of aldonic acids per unit of enzyme. When employing the process of the invention, it is found that the enzymes employed have increased lifetimes.

The aldonic acids and their salts, obtained in accordance with the process of the invention, can be used for cleaning metals, for cleaning bottles, as a sequestering agent and for manufacturing pharmaceutical products and foodstuffs.

The following examples are given in order to demonstrate the advantages of the process according to the invention, compared with the conventional processes. Experiments 1, 5, 6 and 12 were carried out by way of comparison and experiments 2, 3, 4, 7, 8, 9 and 10 were carried out according to the invention.

OXIDATION OF GLUCOSE WITH THE AID OF GLUCOSE OXIDASE

EXAMPLE 1 (COMPARISON)

The enzyme employed is a technical-grade glucose oxidase having a catalase activity, which is supplied by the company SIGMA CHEMICAL Co. and contains 15,000 international units of enzyme per gram. The enzyme was immobilised in the form of a foam in accordance with the technique described in the article by G. BROUN, D. THOMAS, G. GELLF, D. DOMURADO, A. M. BEFJONNEAU and C. GUILLON, Biotechnology and Bioengineering, Volume XV, pages 359-375 (1973).

The experiments were carried out in a 200 cm$^3$ glass reactor provided with an overflow and a stirrer and having a useful volume of 100 cm$^3$. The reactor is kept at a temperature of 25° C.

35 mg of immobilised glucose oxidase and 100 cm$^3$ of a solution containing 37.8 g.liter$^{-1}$ of glucose and 0.01 mol.liter$^{-1}$ of a phosphate buffer of pH 6.8 are placed in the reactor.

Oxygen under atmospheric pressure is bubbled continuously through the solution. The glucose content of the solution is kept constant by continuously adding a solution containing 410 g.liter$^{-1}$ of glucose. The molar ratio of oxygen to glucose is about 0.0059 throughout the reaction.

The pH of the solution is kept constant by continuously adding a solution containing 1 mol.liter$^{-1}$ of sodium hydroxide, which has been saturated beforehand with oxygen at atmospheric pressure. The gluconic acid is thus neutralised to give sodium gluconate.

The overflow is collected continuously and the sodium gluconate therein is determined.

After 6.6 hours of operation, 2.94 g of glucose have been oxidised, which corresponds to 5.6 mg of glucose converted per international unit of glucose oxidase employed.

EXAMPLE 2

The enzyme employed is identical to that used in Example 1. The enzyme was immobilized on granules of pumice stone, having a particle size of between 0.5 and 1 mm, in accordance with the technique described below.

151.5 mg of glucose oxidase are dissolved in 54 ml of an aqueous solution of phosphate buffer. A solution of 8.4 g of albumin in 42 ml of the phosphate buffer is prepared at the same time. After the albumin has completely dissolved, the solutions are mixed and 54 ml of a buffered solution containing 810 mg of glutaraldehyde are added.

After homogenisation, 170 g of pumice stone are added. The resulting mixture is subjected to a vacuum in order to remove the occluded air and, after return to atmospheric pressure, it is kept at −35° C. for about 4 hours. The product is then brought back to ambient temperature and washed with a solution of glycine and then with a solution of phosphate buffer.

The experiments were carried out in equipment of the same type as that shown in FIG. 2.

The glucose oxidase immobilised on the pumice stone is placed in a 300 cm$^3$ reactor kept at 25° C. A solution containing 40 g.liter$^{-1}$ of glucose is introduced into the mixer at a rate of 850 mg of glucose per hour. The solution is saturated with pure oxygen at atmospheric pressure. The pH is kept at 7.6 by adding an aqueous solution containing 1 mol.liter$^{-1}$ of sodium hydroxide.

The recycled solution circulates in the reactor at a rate of 10 liters.hour$^{-1}$. The average glucose content of the recycled solution is 800 mg.liter$^{-1}$, which corresponds to a molar ratio of glucose to dissolved oxygen of 3.6.

After 42 hours, 42 g of glucose have been converted, that is to say 18.5 mg of glucose per unit of glucose oxidase.

EXAMPLE 3

The enzyme employed is identical to that used in Example 1. 1.29 g of enzyme were immobilised on 2.4 kg of granules of titanium sponge, having a particle size of between 1 and 2 mm, in accordance with the technique described in the abovementioned patent application.

The experiments were carried out in equipment of the same type as that shown in FIG. 1.

The glucose oxidase immobilised on the titanium sponge is placed in a 4 liter reactor kept at 25° C. A solution containing 41 g.liter$^{-1}$ of glucose is introduced continuously into the recycled solution via 3 at a rate of 1.3 g of glucose per hour. The solution is saturated at 6 with pure oxygen at a pressure of 2.45 bars. The pH is kept at 6.88 by adding, via 9, an aqueous solution containing 1 mol.liter$^{-1}$ of sodium hydroxide.

The recycled solution circulates in the reactor at a rate of 10 liters.hour$^{-1}$. The average glucose content of the recycled solution is 90 mg.liter$^{-1}$, which corresponds to a molar ratio of glucose to dissolved oxygen of 0.16.

After 750 hours of operation, 980.4 g of glucose have been converted, that is to say 51 mg of glucose per unit of glucose oxidase.

EXAMPLE 4

The enzyme employed is identical to that used in Example 1. 1 mg of enzyme was immobilised on 40 g of granules of pumice stone in accordance with the technique described in Example 2.

A solution containing 1 g.liter$^{-1}$ of glucose, saturated with pure oxygen under a pressure of 20.6 bars, is prepared in a pressure-resistant metal mixer/saturator. The pH of the solution is kept at 6.88 by virtue of the presence of a phosphate buffer at a concentration of 0.1 mol.liter$^{-1}$.

The solution is introduced continuously, at a rate of 40 ml.hour$^{-1}$, into a 50 cm$^3$ metal reactor, kept at 25° C., in which the immobilised enzyme has been placed. The reactor is kept under a pressure of about 21 bars.

The average glucose content of the solution in the reactor is 470 mg.liter$^{-1}$, which corresponds to a molar ratio of glucose to dissolved oxygen of about 0.1.

After 280 hours, 3.63 g of glucose have been converted, that is to say 242 mg of glucose per unit of glucose oxidase.

The results of experiments 1 to 4 are recorded in Table I below.

TABLE I

| Example | Amount of glucose converted per unit of enzyme, mg | $\frac{(oxygen)}{(glucose)}$ mol/mol | Pressure of $O_2$, bars |
|---|---|---|---|
| 1(comparison) | 5.6 | 0.0059 | 1.01 |
| 2 | 18.5 | 0.278 | 1.01 |
| 3 | 51 | 6.25 | 2.45 |
| 4 | 242 | 10 | 20.6 |

Examination of Table I shows that, by using molar ratios of oxygen to glucose of more than 0.1, the amount of glucose converted per unit of enzyme is substantially increased. The higher the pressure, the greater is this increase.

EXAMPLE 5 (COMPARISON)

The enzyme employed is a different technical-grade glucose oxidase from that used in Examples 1 to 4; it has a catalase activity, is supplied by the company SIGMA CHEMICAL Co. and contains about 45,000 international units of enzyme per gram.

8.1 g of enzyme were immobilised on 2.4 kg of granules of titanium sponge in accordance with the technique described in the abovementioned patent application.

The experiments were carried out in equipment of the same type as that shown in FIG. 1.

The immobilised glucose oxidase is placed in a 4 liter reactor kept at 25° C. A solution containing 690 g. liter$^{-1}$ of glucose is introduced continuously via 3 at a rate of 6.5 g of glucose per hour. The solution is saturated with pure oxygen at a pressure of 2.45 bars. The pH is kept at 5.6 by adding, via 9, an aqueous solution containing 10 mols.liter$^{-1}$ of sodium hydroxide.

The recycled solution circulates in the reactor at a rate of 100 liters.hour$^{-1}$. The average glucose content of the recycled solution is 7.7 g.liter$^{-1}$, which corresponds to a molar ratio of glucose to dissolved oxygen of 13.7.

After 180 hours of operation, 1,215 g of glucose have been converted, that is to say 3 mg of glucose per unit of glucose oxidase.

EXAMPLE 6 (COMPARISON)

The enzyme employed is identical to that used in Example 5. 20 mg of the enzyme glucose oxidase were immobilised on 16 g of titanium sponge in accordance with the technique described in the abovementioned patent application.

The experiments were carried out in equipment of the same type as that shown in FIG. 2.

The immobilised glucose oxidase is placed in a 30 cm$^3$ reactor kept at 25° C. A solution containing 227 g.liter$^{-1}$ of glucose is introduced into the mixer at a rate of 963 mg of glucose per hour. The solution is saturated with pure oxygen at atmospheric pressure. The pH is kept at 5.6 by virtue of the presence, in the glucose solution, of a buffer (potassium phthalate+sodium hydroxide) at a concentration of 0.5 mol.liter$^{-1}$.

The recycled solution circulates in the reactor at a rate of 3.5 liters.hour$^{-1}$. The average glucose content of the recycled solution is 40 g.liter$^{-1}$, which corresponds to a molar ratio of glucose to dissolved oxygen of 160.

After 10 hours of operation, 3.3 g of glucose have been converted, that is to say 3.1 mg of glucose per unit of enzyme.

EXAMPLE 7

The enzyme employed is identical to that used in Example 5. 20 mg of the enzyme glucose oxidase were immobilised on 16 g of titanium sponge in accordance with the technique described in the abovementioned patent application.

The experiments were carried out in equipment of the same type as that shown in FIG. 2.

The immobilised glucose oxidase is placed in a 30 cm$^3$ reactor kept at 25° C. A solution containing 24.1 g. liter$^{-1}$ of glucose is introduced into the mixer at a rate of 100 mg of glucose per hour. The solution is saturated with pure oxygen at atmospheric pressure. The pH is kept at 5.6 by adding an aqueous solution containing 1 mol.liter$^{-1}$ of sodium hydroxide.

The recycled solution circulates in the reactor at a rate of 1.5 liters.hour$^{-1}$. The average glucose content of the recycled solution is 450 mg.liter$^{-1}$, which corresponds to a molar ratio of glucose to dissolved oxygen of 2.

After 60 hours, 5.17 g of glucose have been converted, that is to say 4.9 mg of glucose per unit of enzyme.

EXAMPLE 8

The enzyme employed is identical to that used in Example 5. 15 g of the enzyme glucose oxidase were immobilised on 2.4 kg of granules of titanium sponge in accordance with the technique described in the abovementioned patent application.

The experiments were carried out in equipment of the same type as that shown in FIG. 1.

The immobilised glucose oxidase is placed in a 4 liter reactor kept at 25° C. A solution containing 670 g.liter$^{-1}$ of glucose is introduced continuously via 3 at a rate of 9 g of glucose per hour. The solution is saturated with pure oxygen at a pressure of 2.45 bars. The pH is kept at 6.88 by adding an aqueous solution containing 10 mols.liter$^{-1}$ of sodium hydroxide.

The recycled solution circulates in the reactor at a rate of 30 liters.hour$^{-1}$. The average glucose content of the recycled solution is 53.1 mg.liter$^{-1}$, which corresponds to a molar ratio of glucose to dissolved oxygen of 0.09.

After 550 hours, 4,530 of glucose have been converted, that is to say 8.4 mg of glucose per unit of glucose oxidase. At the end of the experiment, the sodium gluconate content of the recycled solution is 300 g.liter$^{-1}$.

EXAMPLE 9

The enzyme employed is identical to that used in Example 5. 10 mg of the enzyme glucose oxidase were immobilised on 1.6 g of titanium sponge in accordance with the technique described in the abovementioned patent application.

A solution containing 1 g.liter$^{-1}$ of glucose, saturated with pure oxygen under a pressure of 20.6 bars, is prepared in a pressure-resistant metal mixer/saturator. The pH of the solution is kept at 5.6 by virtue of the presence of a phthalate buffer (potassium phthalate+sodium hydroxide) at a concentration of 0.1 mol.liter$^{-1}$.

The solution is introduced continuously, at a rate of 60 mg of glucose per hour, into an approximately 2 cm$^3$ metal reactor, kept at 25° C., in which the immobilised enzyme has been placed. The reactor is kept under a pressure of 21 bars.

Part of the mixture originating from the reactor constitutes the production, whereas the other part is recycled continuously into the reactor. The flow rate of this recycled solution is 2.2 liters.hour$^{-1}$.

The average glucose content of the solution in the reactor is 400 mg.liter$^{-1}$, which corresponds to a molar ratio of glucose to dissolved oxygen of about 0.08.

After 600 hours, 14.7 g of glucose have been converted, that is to say 34 mg of glucose per unit of glucose oxidase.

The results of experiments 5 to 9 are recorded in Table II below.

TABLE II

| Example | Amount of glucose converted per unit of enzyme, mg | (oxygen)/(glucose) mol/mol | Pressure of $O_2$, bars |
|---|---|---|---|
| 6 (comparison) | 3.1 | 0.0062 | 1 |
| 5 (comparison) | 3 | 0.073 | 2.5 |
| 7 | 4.9 | 0.5 | 1.01 |
| 8 | 8.4 | 11.1 | 2.45 |
| 9 | 34 | 12.5 | 20.6 |

Examination of Table II shows that, by using molar ratios of oxygen to glucose of more than 0.1, the amount of glucose converted per unit of enzyme is substantially increased. The higher the pressure, the greater is this increase.

EXAMPLE 10

The enzyme employed is a different technical-grade glucose oxidase from those used in Examples 1 to 4 and 5 to 9; it has a catalase activity and contains about 500 international units of enzymatic activity per cm$^3$ of its aqueous solution. The enzyme was immobilised by freezing, at −35° C. for 4 hours, a mixture containing 4 ml of this solution of glucose oxidase, 4 ml of 1.5% strength glutaraldehyde solution, 3.2 ml of 20% strength bovine albumin solution and 2 ml of a 0.02 molar phosphate buffer solution of pH 6.88. The product is then brought back to ambient temperature, ground and washed with a solution of glycine.

The resulting product is in the form of a foam which is dispersed in a 500 cm$^3$ glass reactor provided with an overflow which is equipped with a fritted plate for preventing losses of immobilised enzyme. 245 cm$^3$ of a solution having a glucose concentration of 10 g/liter and a pH of 5.6 are then introduced into the reactor. This concentration and this pH are kept constant throughout the experiment by continuously introducing glucose, in the form of an aqueous solution containing 100 g/liter, and a solution of sodium hydroxide containing 1 mol/liter.

The whole is kept at 5° C. and pure oxygen under atmospheric pressure is bubbled through continuously. The molar ratio of oxygen to glucose is about 30 throughout the reaction.

The overflow is collected continuously and the sodium gluconate formed is determined therein.

After 300 hours of operation, 120 g of glucose have been oxidised, which corresponds to 60 mg of glucose converted per international unit of glucose oxidase employed.

OXIDATION OF MIXTURES OF GLUCOSE AND FRUCTOSE

EXAMPLE 11

The enzyme employed is a technical-grade glucose oxidase having a catalase activity, which is supplied by the company SIGMA CHEMICAL Co. and contains about 45,000 international units of enzyme per gram.

20 mg of enzyme were immobilised on 16 g of granules of titanium sponge, having a particle size of between 1 and 2 mm, in accordance with the following technique.

20 mg of glucose oxidase are dissolved in 4 ml of an aqueous solution of phosphate buffer of pH 6.88.

A solution of 640 mg of albumin in 3.2 ml of the phosphate buffer is prepared at the same time.

After the albumin has completely dissolved, the solutions are mixed and 4 ml of a buffered solution containing 60 mg of glutaraldehyde are added.

After homogenisation, the titanium sponge is added. The resulting mixture is subjected to a vacuum in order to remove the occluded air and, after return to atmospheric pressure, it is kept at −35° C. for about 4 hours. The product is then brought back to ambient temperature and washed with a solution of glycine and then with a solution of phosphate buffer.

The experiments were carried out in equipment of the same type as that shown in FIG. 1.

The glucose oxidase immobilised on the titanium sponge is placed in a 30 cm$^3$ reactor kept at 25° C. A solution containing 25 g.liter$^{-1}$ of glucose and 25 g.liter$^{-1}$ of fructose is introduced continuously into the recycled solution via 3 at a rate of 115 mg of glucose and 115 mg of fructose per hour. A solution containing 1.5 g.liter$^{-1}$ of catalase and 15% of glycerol, 5% of sodium citrate, 5% of ethyl alcohol and 5% of sodium chloride is simultaneously added to the recycled solution at a rate of 25,000 international units of enzyme per hour.

The liquid which circulates continuously is saturated at 6 with pure oxygen at atmospheric pressure. The pH is kept at 5.6 by adding, via 9, an aqueous solution containing 1 mol.liter$^{-1}$ of sodium hydroxide.

The recycled solution circulates in the reactor at a rate of 1.5 liters.hour$^{-1}$. The average glucose content of the recycled solution is 730 mg.liter$^{-1}$, which corresponds to a molar ratio of glucose to dissolved oxygen of 3.2.

After 210 hours of operation, 22.6 g of glucose have been converted, which corresponds to 20.8 mg of glucose per unit of glucose oxidase.

EXAMPLE 12 (COMPARISON)

The experiment is carried out in the same reactor as that used in Example 10, in the presence of the same amounts of enzyme immobilised in the same manner.

A solution containing 250 g.liter$^{-1}$ of glucose and 250 g. liter$^{-1}$ of fructose is introduced continuously into the recycled solution via 3 at a rate of 1 g of glucose and 1 g of fructose per hour. A solution containing 1.5 g.liter$^{-1}$ of catalase and 15% of glycerol, 5% of sodium citrate, 5% of ethyl alcohol and 5% of sodium chloride is simultaneously added to the recycled solution at a rate of 25,000 international units of enzyme per hour.

The liquid which circulates continuously is saturated at 6 with pure oxygen at atmospheric pressure. The pH is kept at 5.6 by adding, via 9, an aqueous solution containing 1 mol.liter$^{-1}$ of sodium hydroxide.

The recycled solution circulates in the reactor at a rate of 1.5 liters.hour$^{-1}$. The average glucose content of the recycled solution is 25 g.liter$^{-1}$, which corresponds to a molar ratio of glucose to dissolved oxygen of 110.

After 20 hours of operation, 8.85 g of glucose have been converted, which corresponds to 8.0 mg of glucose per unit of glucose oxidase.

Comparison of experiment 11, carried out with a molar ratio of oxygen to glucose of 0.31, and experiment 12, carried out with a molar ratio of oxygen to glucose of 0.0091, shows that, respectively, 20.8 mg and 8.0 mg of glucose are converted per unit of enzyme, that is to say that the amount of glucose converted per unit of enzyme is substantially increased by operating according to the invention.

What is claimed is:

1. A process for the manufacture of gluconic acid from glucose, comprising enzymatically oxidizing the glucose in the presence of glucose oxidase, in a reaction mixture containing water as a solvent, and containing dissolved oxygen in a concentration of between 40 and 10,000 mg/liter, wherein the oxidation is carried out at a temperature of between 0° and 60° C. and at a pH of between 4.2 and 8, and wherein the molar ratio of dissolved oxygen to glucose in the reaction mixture is kept above 0.1 by application of a gas containing oxygen under an oxygen partial pressure of between 1 and 100 bar.

2. A process according to claim 1, wherein the molar ratio of oxygen to glucose is kept between 0.2 and 50.

3. A process according to claim 1 or 2, wherein the partial pressure is kept between 3 and 80 bars.

4. A process according to claim 1 or 2, wherein the glucose oxidase is in the immobilized form.

5. A process according to claim 1 or 2, wherein said glucose is present in a mixture containing glucose and fructose, and the glucose is oxidized selectively.

* * * * *